United States Patent [19]

Ishii

[11] 4,103,687
[45] Aug. 1, 1978

[54] USE OF HAPTOGLOBIN FOR THERAPY OF CEREBRAL VASOSPASM

[75] Inventor: Shozo Ishii, Tokyo, Japan

[73] Assignee: The Green Cross Corporation, Osaka, Japan

[21] Appl. No.: 707,069

[22] Filed: Jul. 20, 1976

[30] Foreign Application Priority Data

Apr. 16, 1976 [JP] Japan ................................. 51-43100

[51] Int. Cl.² ...................... A61M 5/00; A61K 29/00
[52] U.S. Cl. ............................ 128/214 R; 260/112 B; 424/9; 424/177; 424/101
[58] Field of Search ............... 128/214 R; 424/9, 101, 424/177; 260/112 B; 3/1.4

[56] References Cited

U.S. PATENT DOCUMENTS 3,898,329 8/1975 Said et al. ............................. 424/177

FOREIGN PATENT DOCUMENTS 2,088,112 1/1972 France ..................................... 424/177
2,409,650 5/1975 Fed. Rep. of Germany ........... 424/101

Primary Examiner—Benjamin R. Padgett
Assistant Examiner—Christine M. Nucker
Attorney, Agent, or Firm—Cushman, Darby & Cushman

[57] ABSTRACT

Haptoglobin is effective for preventing and remedy of human cerebral vasospasm when it is applied to spastic cerebral artery of the patient who is or has been suffering from cerebral vasospasm.

12 Claims, 17 Drawing Figures

M: METHYSERGIDE (5μg/ml)
r: RINSE WITH ARTIFICIAL CSF-SOLUTION

M: METHYSERGIDE (5μg/mL)
r: RINSE WITH ARTIFICIAL CSF-SOLUTION

FIG. 4C r: RINSE WITH ARTIFICIAL CSF-SOLUTION

Hb-HP COMPLEX

FIG. 7B r: RINSE WITH ARTIFICIAL CSF-SOLUTION

FIG. 7C

TIME (HOURS)

FIG. 9

1 Day before OP.   Immediately after OP.   3rd Day after OP.

USE OF HAPTOGLOBIN FOR THERAPY OF CEREBRAL VASOSPASM

This invention relates to the prophylaxis and therapy of cerebral vasospasm caused by intracranial hemorrhage, particularly subarachnoid hemorrhage accompanying ruptured aneurysm, characterized by administration of a preparation comprising human serum- or plasma-derived haptoglobin as principal ingredient.

The subarachnoid hemorrhage is bleeding in the cavity between arachnoid and pia, that is, subarachnoid space, and is one of the cases of apoplexia in a broad sense. The principal cause of subarachnoid hemorrhage in the rupture of aneurysm. Of the apoplexia, the ruptured aneurysm is rather frequent among young or middle-aged people and when properly treated successful rehabilitation without any significant symptom of neurological deficit is possible in many cases. Accordingly, in the domain of neurosurgery, the ruptured aneurysm has become one of the most important subjects of cerebrovascular disorders.

For the treatment of ruptured aneurysm, it is desirable, at present, that a radical operation (i.e. clipping of aneurysm) be performed as early as possible in order to prevent recurrent hemorrhage. However, the most important factor to be taken into account in deciding the opportunity of this operation is the phenomenon of cerebral vasospasm. The cerebral vasospasm is said to afflict 30 to 60% of the patients suffered from subarachnoid hemorrhage and the symptoms are developed in about 3 or 4 days after occurrence of the hemorrhage and last for a period of about two weeks. It has been believed undesirable in view of mortality as well as morbidity to operate on a patient while the patient is being afflicted with cerebral vasospasm and clinical symptoms are also getting worse. It is usual practice to postpone the operation until remission of the cerebral vasospasm is induced by conservative treatment. Such an intentionally delayed surgery is, at present, a common treatment for the subarachnoid hemorrhage. It is needless to say, however, that the earlier the operation is performed, the less is the danger of recurrent hemorrhage. There has been reported a high percentage of cases where the patient, before the operation, took a turn for the worst, because of recurrent hemorrhage during the period of conservative treatment or because of serious cerebrovascular disorder following the subarachnoid hemorrhage. Therefore, advent of a medical preparation for prophylaxis and treatment of cerebral vasospasm has been eagerly awaited by many of the people concerned in order to prevent re-hemorrhage by early surgery.

There still remains a great deal of obscurity about the mechanism of induction of the cerebral vasospasm.

It has quite recently been demonstrated photographically or augiographically in animal experimental model that cerebral vasospasm may be artificially induced by allowing blood constituents to act directly on an exposed basilar artery or by injecting blood into subarachnoid space. Based on these facts, it might be presumed that the blood leaked out of a blood vessel plays an important role in the induction of cerebral vasospasm.

On the other hand, there is, at present, practically no effective means for treating cerebral vasospasm. For the purpose of investigational treatment, there has, heretofore, been tried local or systemic administration of vasodilators such as papaverine, procaine, and lidocaine, sympathetic nerve drugs such as phenoxybenzamine, phentolamine, and isoproterenol, serotonin antagonists, antihistaminics, dibutyryl cyclic AMP, and ethyl alcohol. Administration of fibrinolytic inhibitors and inhalation of carbon dioxide have also been tried for the purpose of preventing fibrinolysis. All of the above-noted drugs have shown only insufficient or transient effects.

An object of this invention is to provide a medical preparation for preventing as well as treating cerebral vasospasm, which, once developed, is difficult to be treated.

Principal causes for the cerebral vasospasm so far presumed are mechanical stimuli, vasoactive substances, stimuli to vasomotor nerves, and the change in vascular smooth muscle cells. Paying special attention to the vasoactive substance, the present inventors carried out biochemical analysis by use of a blood-cerebrospinal fluid mixture (blood-csf mixture) to incover the role played by said mixture in cerebral vasospasm. As the result, it was found that the substance responsible for the early spasm is serotonin or analogs thereof and the cerebral vasospasm due to these substances is completely controlled by serotonin antagonists. It was further found that the late spasm, that is, cerebral vasospasm which is the subject of this invention, is induced by oxyhemoglobin or a polypeptide having biochemical properties bearing a close resemblance to those of oxyhemoglobin, which is set free by hemolysis of the red corpuscle, and can be effectively treated with local administration of haptoglobin or a hemoglobin-haptoglobin complex. These findings have led to the accomplishment of the present invention. The vasospasmodic effect of oxyhemoglobin was observed specifically on cerebral artery and not at all on, for example, mesenteric artery.

HbBC as used hereinafter is an abbreviation for "Hemoglobin Binding Capacity". One unit of haptoglobin combines with 1 mg of hemoglobin.

Haptoglobin or hemoglobin-haptoglobin complex is used for the therapy of cerebral vasospasm according to the following methods:

1. At the surgery of the ruptured aneurysm: Local application of Haptoglobin upon the spastic cerebral artery is the most effective method to release the prolonged vasospasm. Each dose of local application is 2 or 3 ml of Haptoglobin solution (20 mg HbBC/ml).

At this time, spastic arteries are soaked in the Haptoglobin solution and is washed out with normal saline.

This procedure is repeated several times during the operation.

The same dose of Haptoglobin is applied upon the spastic cerebral artery prior to the closure of the dura mater.

After surgery, infusion of Haptoglobin (2 ml/mol – 10 mg HbBC/ml) is repeated for two days through a catheter left in the basal cistern.

2. At the early surgery of the ruptured aneurysm: 100 ml of Haptoglobin solution (20 mg HbBC/ml) is diluted with 500 ml of normal saline. After clipping of the neck of aneurysm is carried out, arteries proximal and distal to the aneurysm are irrigated by this diluted haptoglobin solution.

3. Other purpose:
    (1) Intraventricular application. Infusion of haptoglobin solution (2 ml of 10 mg HbBC/ml) is repeated several times through a shunting tube or external drainage tube.

(2) Intrathecal application. Haptoglobin solution (2 ml of 10 mg HbBC/ml) is injected into the spinal subarachnoid space.

(3) Haptoglobin is effective to prevent the prolonged spasm after massive hemorrhage in the basal cistern at any operation.

The invention and advantages thereof are illustrated below with reference to Experimental Examples and Clinical tests. Brief explanation of the accompanying drawings which are cited in Experimental Examples and Clinical tests is given below.

BRIEF DESCRIPTION OF THE DRAWINGS

FIG. 1

A. The apparatus used for preparing an arterial strip, herical strip was cut from the threaded artery as needle rotates.

B. Arterial strip was suspended in plastic chamber containing oxygen saturated artificial CSF solution at 37° C. Reagent was applied into this chamber and mixed by magnetic stirrer.

FIG. 2 Typical response of basilar artery to the aged serum (0, 1, 4, and 7 days at 37° C).

A. Vasoactivity of serum was decreased quickly as aging continued and over 4 days incubated samples were essentially non-vasoactive, contraction induced by fresh serum was most obvious and was nearly equal by scrotonin (5 μg/ml).

B. Serum induced contraction was completely antagonized by methysergide, scrotonin antagonist. Antagonist was added to the bath 3 min. before the agonist.

FIG. 3 Typical response of basilar artery to the supernatant of blood-CSF mixture.

A. Vasoactivity of blood-CSF mixture was progressively increased as aging continued. Contraction induced by incubated sample for 7 days was most obvious and nearly equal to that by scrotonin.

B. Contraction induced by supernatant of aged blood-CSF mixture was not antagonized by methysergide. Antagonist was added to the bath 3 min. before the agonist.

FIG. 4 Contraction of basilar artery induced by supernatants of aged blood-CSF mixture.

A. One of the most characteristic contraction, tonic tension superimposed with phasic contraction, it usually lasted for several hours.

B. This contraction was not subsided easily by washing arterial strip with artificial CSF solution.

C. Contraction was further enhanced markedly under the hypoxic condition produced by the cessation of continuous oxygen supply into the bath and returned quickly to the previous level when oxygen was resaturated.

FIG. 5

A. Sephadex G-100 column chromatography of blood-CSF mixture. Left; fresh sample. Right; incubated sample for 7 days. The 3rd peak was markedly increased as aging continued.

B. Vasoactivity of these 3 peaks of incubated sample for 7 days. Third peak had strong vasoactivity.

FIG. 6 Vasospasm produced by the incubated blood-CSF mixture. Left vertebral angiogram Left:—Control angiogram Middle:—10 days after injection of concentrated fraction of peak III of sephadex G-100 to the basal cistern.

Right:—16 days after injection to the basal cistern. Marked diffuse late spasm developed at the basilar artery and the circle Willis.

FIG. 7 Contraction induced by Hb. or its allied polypeptide was inhibited by application of haptoglobin.

A. When Hb. combined to Hp., the vasoactivity of Hb. was markedly abolished.

B. No further contraction developed by adding Hb. or its allied polypeptide after application Hb.-Hp. complex.

C. When haptoglobin or Hp-Hb were applied to the arterial strip which had maximally contracted by free hemoglobin, contraction reduced for some extent.

FIG. 8 Spasmolytic effect of Hp.

Left:—Control vertebral angiogram.

Middle:—2 days after injection of Hb. to the basal cistern, diffuse vasospasm developed.

Right:—After confirming the development of spasm, Hp. was injected to the basal cistern and 5 hours after this vasospasm became markedly reduced.

FIG. 9

Left:—1 day before operation marked vasospasm has been demonstrated at the $M_1$ and $M_2$.

Middle:—Immediately post operative angiogram after treatment by Haptoglobin reduced at this segment.

Right:—3rd day after operation.

The haptoglobin preparation used herein, which was supplied by The Green Cross Corporation, Japan, was a brownish liquid prepared according to Japanese Pat. applications Laid-open (Kokai) No. 77516/75 and No. 77527/75 (U.S. Pat. application No. 677,085), by purification of $\alpha_2$-globulin obtained by fractionation from $\alpha$- and $\beta$-globulin fraction of human blood plasma. The method is characterized by subjecting an aqueous solution of $\alpha$- and $\beta$-globulin fractions of human blood plasma to further fractionation by use of ammonium sulfate, collecting fractions precipitated at ammonium sulfate concentration between 30% W/V and 40% W/V saturation, contacting an aqueous reconstituted solution of the collected fractions with a strong anion exchanger to adsorb haptoglobin onto said anion exchanger, eluting haptoglobin from the anion exchanger, concentrating the resulting eluate and, if necessary, forming the concentrated solution into a physiologically acceptable aqueous solution. Further, the solution is inactivated in HB-Ag by adding at least one stabilizer selected from the group consisting of neutral amino acids, monosaccharides, disaccharides and soluble sugaralcohols to the aqueous solution of haptoglobin after any of the steps of the above process and heating the mixture until HB-Ag is inactivated and then freed from the stabilizer. The composition of the preparation used contains 2,000 units of human plasma haptoglobin (one unit of haptoglobin combines with 1 mg of hemoglobin) and 0.90 g of sodium chloride in one vial (100 ml), and haptoglobin purity is 90% or more of haptoglobin ($\alpha_2$-globulin) with a minute amount of $\beta$-globulin, as measured by electrophoresis.

The preparation is less than 10% in hypotensive activity, highly stable during storage and free from hepatitis B virus (HB-Ag).

Experimental Example

Materials and Methods

Figure 1A:
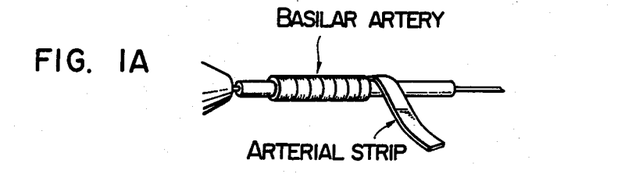
Figure 1B:
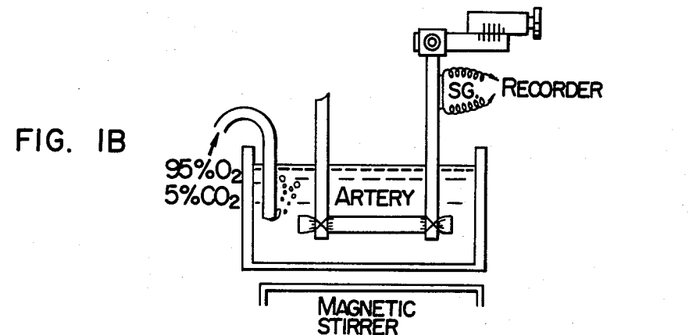

Basilar artery of 10 – 15 kg adult dog was revolved immediately after the animal was sacrificed. According to the Speden's method, (Speden, R.N., J. Physiol. 154, 15 – 25, 1960) a spirally cut strip of basilar artery was prepared (FIG. 1A). This strip was mounted in a plastic chamber filled with 5 cc of artificial CSF (NaCl 128 mM, NaHCO$_3$ 15 mM, KCl 1.8 mM, KH$_2$PO$_4$, MgSO$_4$ 1.3 mM, CaCl$_2$ 1.3 mM, Glucose 1.5 mM). One end of the arterial strip was fixed and the other end was tied to a clamp with a sliding scale which was connected to the strain gauge. Isometric tension of the arterial strip was recorded with electronic pen writer. (FIG. 1B). The solution was oxygenated with 95% O$_2$ and 5% CO$_2$ gas mixture throughout the experiment. pH was kept at 7.4 and fluid temperature was maintained at 37° C. Vasoactivity of fresh or aged specimens of serum, whole blood and blood-CSF mixture (1 : 1, 1 : 4) upon the isolated artery was tested by adding 0.1 – 0.5 ml of each test sample to the medium. Aging of samples was made by incubating them at 37° C for 0 to 7 days under the aseptic condition.

For the purification of vasoactive substances samples were first gel-filtrated using a Sephadex G-100 column chromatography (2.5 × 90 cm) eluted with 0.1 M tris-HCl (pH 8.0) containing 1M NaCl. The ninhydrin reaction and the absorbance at 280, 415 m$\mu$ were measured, and fraction which possessed the vasoactivity was collected. Then the fraction was further purified using Carboxyl-Methyl cellulose ion exchange resin column chromatography (2.5 × 40 cm) eluted with 0.01 M phosphate buffer, pH 7.0, containing 0.5 M NaCl. The analysis of the polypeptide contained in the vasoactive fraction was carried out using polyacryl amide gel electrophoresis according to the method of Orstein (Orstein; L: Ann. N.Y. Acad. Sciences, 121 321–349, 1969).

Results and Discussion

Figure 2A:
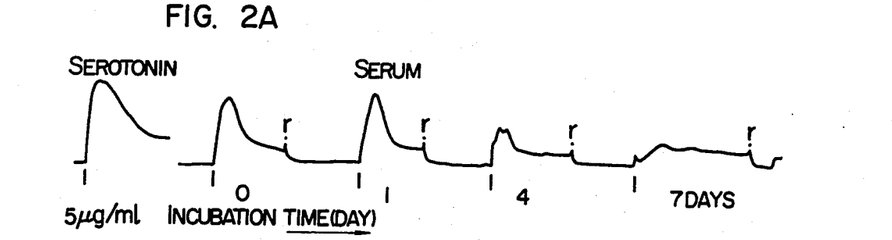
Figure 2B:
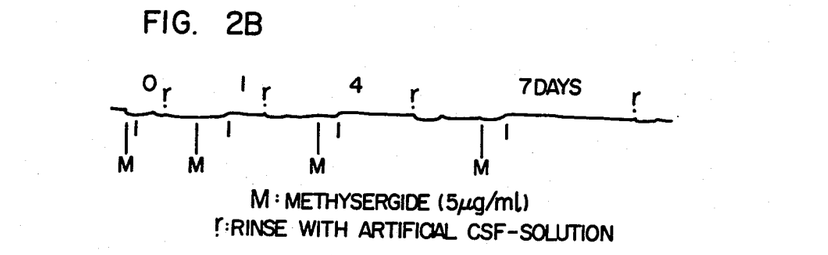

Contraction of artery produced by serum was most obvious in fresh sample and decreased quickly as aging continued. This serum aged over 7 days was essentially non-vasoactive (FIG. 2A). Also, serum-induced contraction was almost completely abolished by methysergide, a serotonin antagonist (FIG. 2B). The contraction induced by serum or serotonin immediately subsided when the strip of artery returned to the previous medium of artificial CSF. These results accorded fairly well to those which had previously been reported, and serotonin or its allied compounds in serum are probably responsible only for the development of early spasm.

Figure 3A:
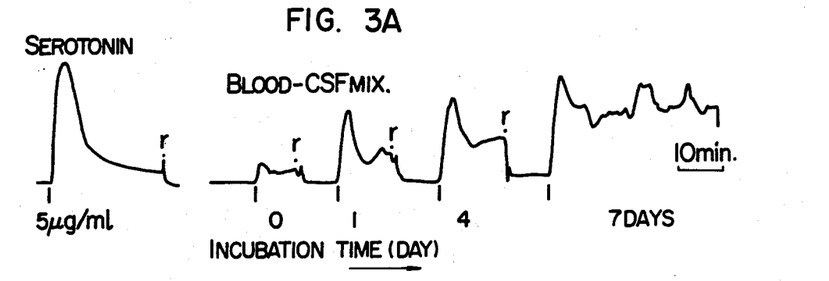
Figure 3B:
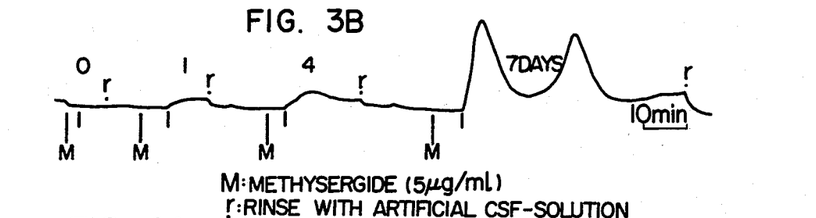
Figure 4A:
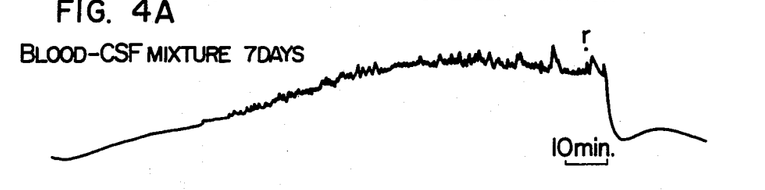
Figure 4B:
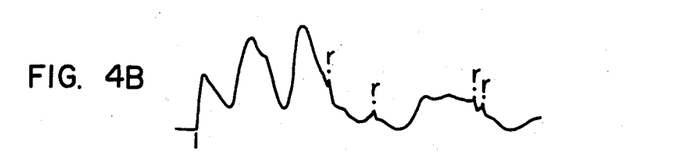
Figure 4C:
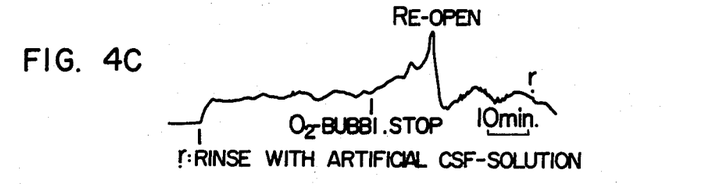

On the other hand, vasoactivity found in supernatants of the incubated whole blood and blood-CSF mixture became progressively increased as aging of samples was continued reaching its peak after approximately 7 days of incubation (FIG. 3A). Moreover, vasoactivity found in supernatant of either aged blood-CSF mixture or aged whole blood remained unchanged by the addition of methysergide (FIG. 3B). Arterial constriction produced by the addition of aged blood-CSF mixture was found to be far greater than that by aged blood alone and it was characterized by tonic tension superimposed with phasic contraction of the isolated basilar artery which usually lasted over several hours (FIG. 4A). Once arterial contraction was induced by these aged samples, it did not subside easily by washing the artery with artificial CSF (FIG. 4B), and these contraction was further enhanced markedly under the hypoxic condition produced by the cessation of continuous O$_2$ supply into the reaction medium (FIG. 4C).

Figure 5A:
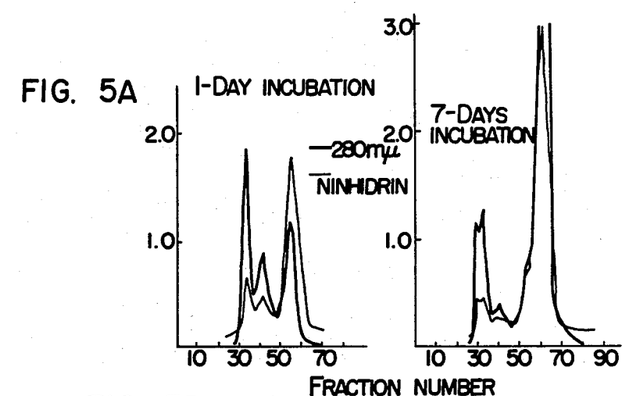
Figure 5B:
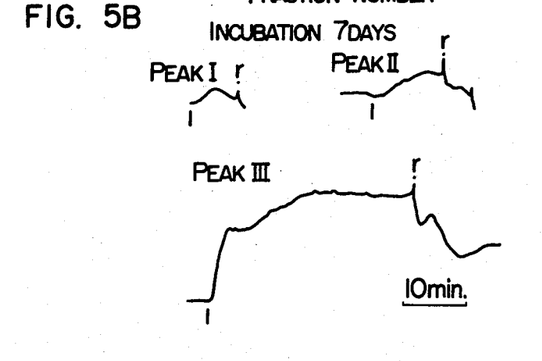
Figure 6:
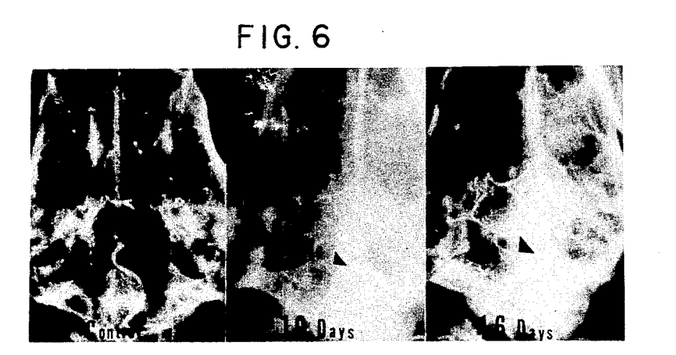

For isolation of the vasoactive substance, supernatant of blood-CSF mixture (1 : 1) which had been incubated for 7 days at 37° C was passed through a column of Sephadex G-100. Vasoactivity was only noticeable at the 3rd peak of the chromatographically eluted fractions (FIG. 5). This vasoactive fraction (Peak III) was collected and concentrated by the diafiltration. The concentrated vasoactive substance was added with appropriate amount of fibrinogen and thrombin. When thin disc of the clot thus formed applied to the ventral surface of the caudal pons of adult dog through the trephine opening made at the midline of clivus, marked vasospasm developed at the vasilar artery and at the circle of Willis. It usually lasted over 2 weeks (FIG. 6).

For the further purification of the vasoactive substance, Peak III was passed through a column of C-M cellulose ion exchange resin. On each fraction eluted, vasoactivity was checked through in vitro experiments and it was found that the vasoactive substance localized at the 3rd peak (Peak III C-M-C). Absorption curve of thie Peak III C-M-C was analyzed with a self-recording spectrophotometer and prominent absorption were found at 415, 540 and 575 millimicra. These were typical for oxyhemoglobin. Another biochemical analysis of Peak III C-M-C using polyacryl amide gel electrophoresis also demonstrated that chemical characteristics of this peak corresponded to those of oxyhemoglobin. Thus, it might be safe to assume that vasoactive substance isolated from blood-CSF mixture seemed to be polypeptides which were closely allied to oxyhemoglobin or oxyhemoglobin itself.

Haptoglobin, $\alpha_2$-globulin, is a normal constituent of serum. It has been known that haptoglobin has the property of binding with hemoglobin stoichiometrically to form a chemically stable haptoglobin-hemoglobin complex quite easily.

Thus, haptoglobin was used and haptoglobin-hemoglobin complex (Hp-Hb) was further prepared by adding haptoglobin to either chromatographically eluted peak III-C-M-C or hemoglobin prepared according to the Drabkin's method and then isolating through gel-filtration.

Figure 7A:
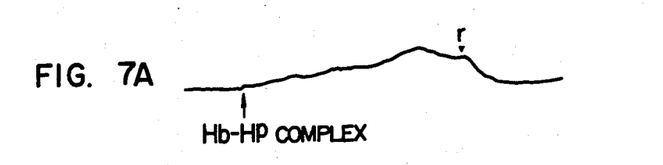
Figure 7B:
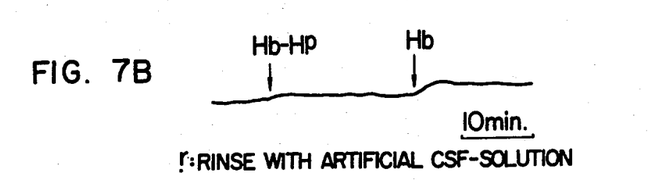
Figure 7C:
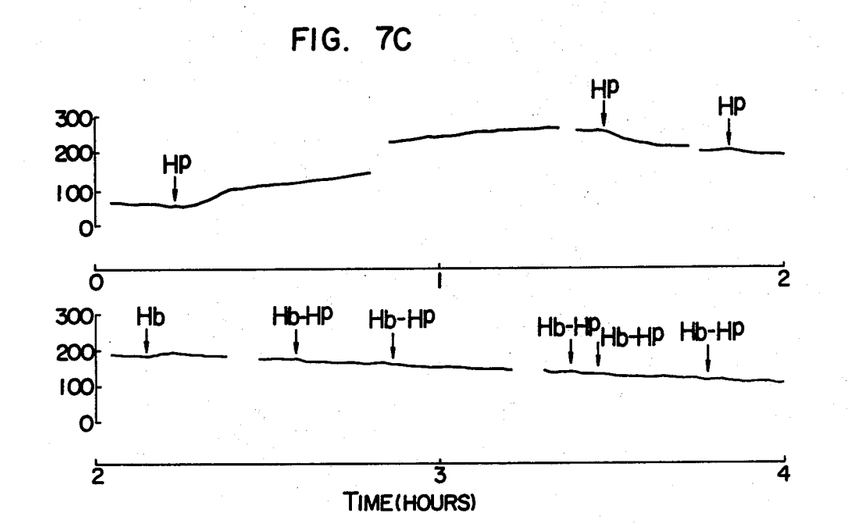

In the next series of in vitro experiments conducted according to the same method as above following were confirmed 1) Contraction induced by Hp-Hb was far less obvious compared to that by free hemoglobin alone (FIG. 7A). Furthermore, when the arterial strip was first treated with Hp-Hb compound it failed to contract by the further addition of free hemoglobin (FIG. 7B), 2) When haptoglobin or Hp-Hb were applied to the arterial strip which had maximally contracted by free hemoglobin, contraction reduced for some extent (FIG. 7C).

Thus, it has been assumed that when hemoglobin or allied polypeptides are liberated through the spontaneous hemolysis of extravasated erythrocytes, they combine with haptoglobin until the capacity of the latter is exhausted. Even when the amount of hemoglobin becomes exceeded beyond the binding capacity of available haptoglobin, and free hemoglobin may accumulate for some extent, vasoactivity of the latter will be blocked by the presence of Hp-Hb. This might be the answer for the question why the vasoactivity exterted by the aged whole blood was far less obvious than that of blood-CSF mixture of same volume despite of the fact that hemoglobin content in the former was greater than the latter. It is also assumed that in case of ruptured aneurysm, extravasated blood is first diluted with CSF then serum will be washed out through CSF circulation leaving comparably large part of blood corpuscles in basal cistern or in the sylvian fissure. The condition like this will provide a favorable milieu for the development of vasospasm because free hemoglobin continues to increase through hemolysis while total amount of haptoglobin has been greatly reduced.

Figure 8:
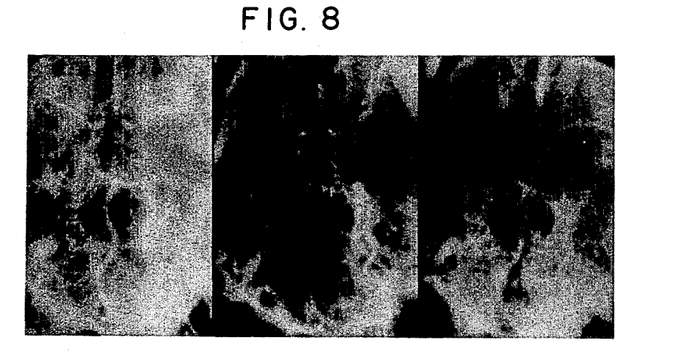

Returning to in vivo experiment, an appropriate amount of hemoglobin was injected into the cisterna magna. Marked vasospasm of basilar artery and circle of Willis did develop and it usually lasted over 4 or 5 days in the control animals. On the 3rd day of injection of free hemoglobin, and after confirming the presence of diffuse vasospasm by angiography, 1 ml of haptoglobin solution (20 mg HbBC/ml) was further injected into the basal cistern. Approximately 5 hours following the injection of haptoglobin, degree of vasospasm became reduced and caliber of arteries returned towards normal (FIG. 8).

Clinical test 1.

Finally, based on these experimental results clinical use of haptoglobin on the vasospasm was made in several patients. One case will be demonstrated here. A 60 years old male had suffered from subarachinoid hemorrhage 7 days prior to his admission. Angiogram taken next day showed a saccular aneurysm at the anterior communicating artery and marked vasospasm at $C_1$, $A_1$ and $M_1$. Two days after his admission clipping of the neck of aneurysm was carried out and spastic arteries were irrigated by 3 ml of haptoglobin solution which contained 20 mg HbBC/ml. Infusion of haptoglobin was repeated for two days following the surgery through a catheter left in the basal cistern. Angiogram made on the 3rd postoperative day demonstrated the obvious release of vasospasm at the circle of Willis.

Clinical test 2.

Figure 9:
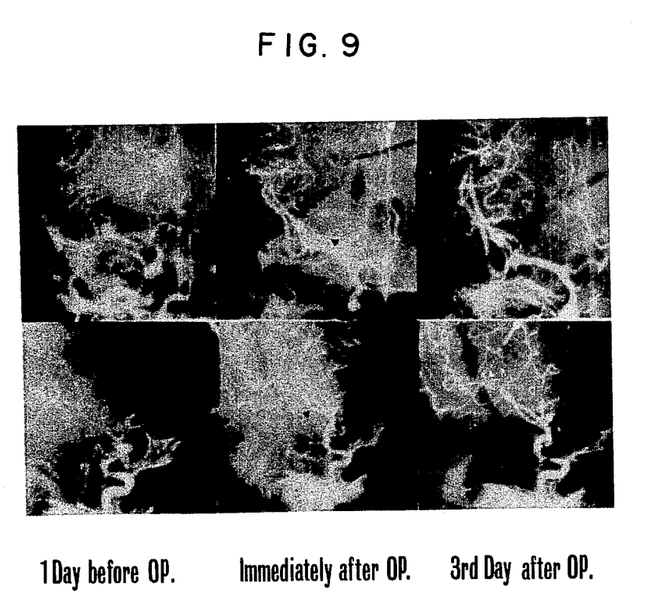

Patient was a 46-year-old female who had two connective ruptures of aneurysm at the middle cerebral artery. Cerebral angiogram was taken on the 14th day following second bleeding. Angiogram showed a saccular aneurysm on the right middle cerebral artery and the marked vasospasm especially at the middle cerebral artery. On the next day she was operated upon and haptoglobin was introduced to the arteries along the Sylvian fissure after the neck of aneurysm was clipped. Arteries in marked spasm dilated immediately after the surgery and they remained dilated for several days as shown in the angiograms taken on the 3rd postoperative day (FIG. 9).

what is claimed is:

1. A method of releasing and remedying human cerebral vasospasm comprising administering to a spastic cerebral artery haptoglobin or haptoglobin-hemoglobin complex in an amount sufficient for such purpose.

2. The method of claim 1, wherein the administration is carried out locally to release the prolonged vasospasm.

3. The method of claim 2, wherein the administration is carried out by soaking spastic arteries in haptoglobin solution.

4. The method of claim 2 wherein there is a ruptured aneurysm and the neck of the aneurysm is clipped off and the administration is carried out by irrigating arteries proximal and distal to the aneurysm with an aqueous haptoglobin solution containing normal saline, after clipping of the neck of the aneurysm, at the early surgery of the ruptured aneurysm.

5. The method of claim 1, wherein the administration is carried out intraventricularly by repeated infusions of haptoglobin solution to release the vasospasm.

6. The method of claim 1, wherein the administration is carried out intrathecally by injecting haptoglobin solution into the spinal subarachnoid space.

7. The method of claim 1, wherein the sufficient amount of haptoglobin is 20 mg HbBC to 60 mg HbBC.

8. The method of claim 3, wherein the spastic arteries to which haptoglobin has been administered are washed with normal saline, and further soaked in haptoglobin solution.

9. The method of claim 1, wherein the haptoglobin used is in the form of an isotonic aqueous solution which is less than 10% in hypotensive activity, high stable during storage and which has been subjected to heat treatment in the prevence of a selected stabilizing agent for inactivating hepatitis B virus.

10. The method of claim 9, wherein the isotonic aqueous haptoglobin solution is prepared by subjecting an aqueous solution of α- and β-globulin fractions of human blood plasma to further fractionation by use of ammonium sulfate, collecting fractions precipitated at ammonium sulfate concentration between 30% W/V and 40% W/V saturation, contacting an aqueous reconstituted solution of the collected fractions with a strong anion exchanger to adsorb haptoglobin onto said anion exchanger, eluting haptoglobin from the anion exchanger, concentrating the resulting eluate.

11. The method of claim 10 including the step of forming the concentrated solution into a physiologically acceptable aqueous solution.

12. The method of claim 11 including the steps of adding at least one stabilizer selected from the group consisting of neutral amino acids, monosaccharides, disaccharides and soluble sugar alcohols to the aqueous solution of haptoglobin after any of the steps of the process and heating the mixture until heptatitus B virus is inactivated and then freeing the haptoglobin or haptoglobin-hemoglobin from the stabilizer.

* * * * *